United States Patent
Duncker et al.

(10) Patent No.: US 9,500,728 B2
(45) Date of Patent: Nov. 22, 2016

(54) SIGNAL ANALYZER FOR NUCLEAR MAGNETIC FLOWMETERS

(71) Applicant: Krohne AG, Basel (CH)

(72) Inventors: Bart Duncker, Eemnes (NL); Jan Johannes Jacobus Hofstede, Gouda (NL); Stephan Inge Luik, Alphen aan de Rijn (NL)

(73) Assignee: Krohne AG, Basel (CH)

( * ) Notice: Subject to any disclaimer, the term of this patent is extended or adjusted under 35 U.S.C. 154(b) by 514 days.

(21) Appl. No.: 14/217,770

(22) Filed: Mar. 18, 2014

(65) Prior Publication Data

US 2014/0285199 A1    Sep. 25, 2014

(30) Foreign Application Priority Data

Mar. 19, 2013 (DE) .......................... 10-2013-004671
Apr. 12, 2013 (DE) .......................... 10-2013-006305

(51) Int. Cl.
*G01V 3/00*      (2006.01)
*G01R 33/36*     (2006.01)
*G01F 1/716*     (2006.01)
*G01N 24/08*     (2006.01)
*G01R 33/563*    (2006.01)

(52) U.S. Cl.
CPC .............. *G01R 33/36* (2013.01); *G01F 1/716* (2013.01); *G01N 24/08* (2013.01); *G01N 24/081* (2013.01); *G01R 33/563* (2013.01)

(58) Field of Classification Search
USPC ........................................................ 324/318
See application file for complete search history.

(56) References Cited

U.S. PATENT DOCUMENTS

| | | | | |
|---|---|---|---|---|
| 3,339,410 | A * | 9/1967 | Marius Steru | G01F 1/58 73/861.16 |
| 3,562,632 | A | 2/1971 | Kirkland | |
| 3,926,049 | A * | 12/1975 | Seebode | G01F 1/60 73/861.12 |
| 3,991,612 | A * | 11/1976 | Mannherz | G01F 1/58 73/861.17 |
| 5,208,537 | A | 5/1993 | Rietsch et al. | |
| 7,773,715 | B2 * | 8/2010 | Westfield | G01D 3/08 340/870.16 |
| 8,571,819 | B2 | 10/2013 | Henry | |
| 8,683,873 | B1 * | 4/2014 | Feller | G01F 1/3209 73/861.23 |
| 9,411,034 | B2 * | 8/2016 | Hofstede | G01R 33/3621 |
| 2009/0289630 | A1 * | 11/2009 | Nascimento | G01R 33/365 324/307 |

FOREIGN PATENT DOCUMENTS

| | | |
|---|---|---|
| DE | 25 08 607 A1 | 9/1996 |
| DE | 196 31 900 A1 | 2/1998 |

\* cited by examiner

*Primary Examiner* — Rodney Fuller
(74) *Attorney, Agent, or Firm* — David S. Safran

(57) ABSTRACT

A signal analyzer for nuclear magnetic flowmeters is provided. The signal analyzer can be placed in a power signal path between a signal generator that generates an electric excitation signal and an electrical load. The signal analyzer includes a power signal line in the power signal path for the transmission of electrical signals. The signal analyzer also includes a decoupling circuit for decoupling a first signal characterizing the excitation signal occurring in the load and for decoupling of a second signal characterizing the part of the excitation signal reflected at the load. The signal analyzer further includes a first attenuator and a second attenuator. Additionally, the signal analyzer includes a detector for determining the ratio of the magnitude of the first signal to the magnitude of the second signal and for determining the phase difference between the first signal and the second signal.

12 Claims, 1 Drawing Sheet

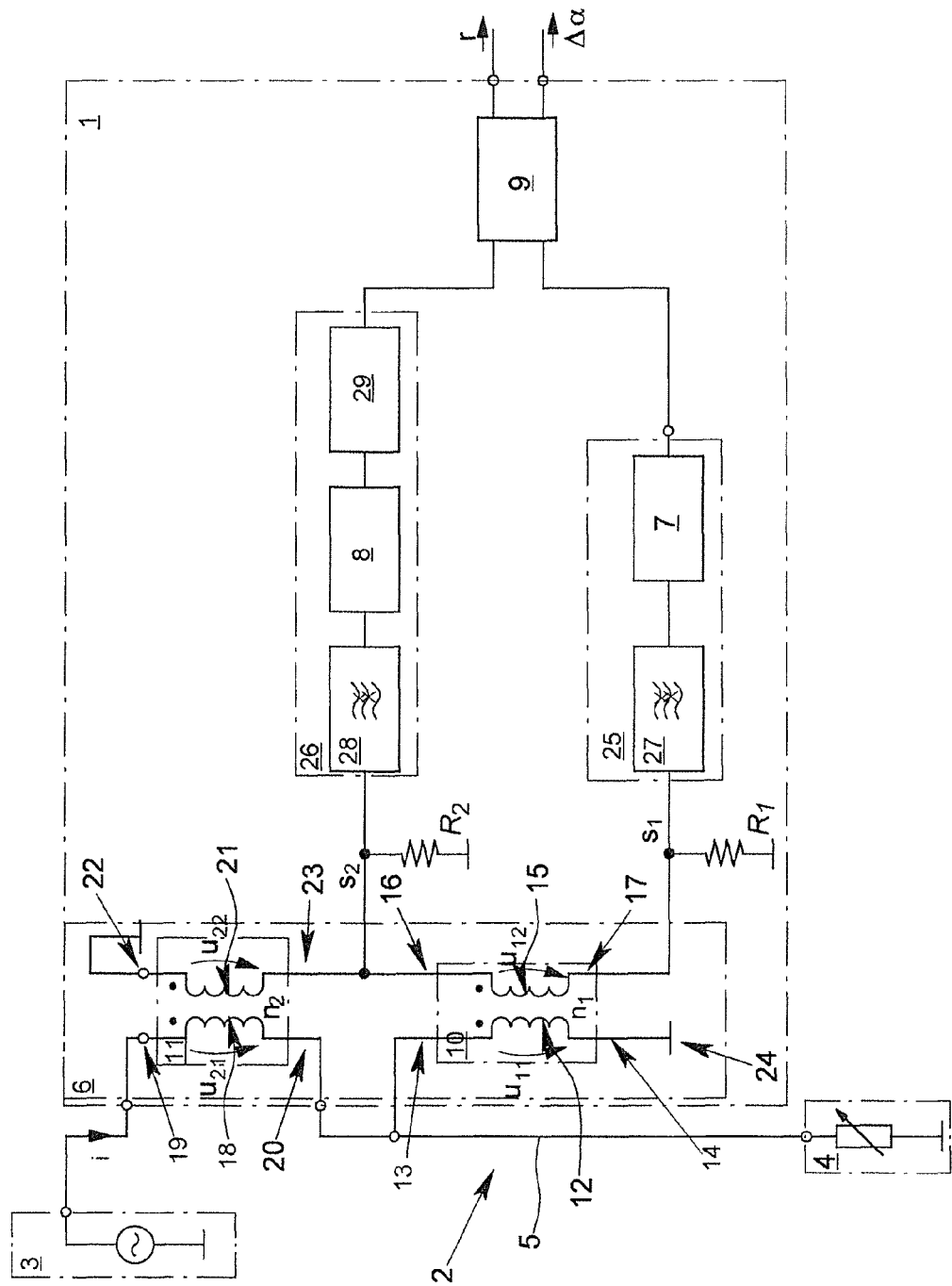

SIGNAL ANALYZER FOR NUCLEAR MAGNETIC FLOWMETERS

BACKGROUND OF THE INVENTION

Field of the Invention

The invention relates to a signal analyzer. More specifically, the invention relates to a signal analyzer for nuclear magnetic flowmeters that is in a power signal path between a signal generator for generating an electric excitation signal and an electrical load. The signal analyzer includes a power signal line in the power signal path for the transmission of electrical signals. The signal analyzer also includes a decoupling circuit for decoupling a first signal characterizing the excitation signal occurring in the load and for decoupling a second signal characterizing part of the excitation signal reflected at the load. The signal analyzer further includes a first attenuator and a second attenuator and having a detector for determining the ratio of the magnitude of the first signal to the magnitude of the second signal and for determining the phase difference between the first signal and the second signal.

Description of Related Art

The atomic nuclei of the elements having nuclear spin also have a magnetic moment caused by the nuclear spin. Nuclear spin can be regarded as angular momentum and can be represented by a vector. Accordingly, the magnetic moment can also be represented by a vector, which is aligned parallel to the vector of the angular momentum. The vector of the magnetic moment of an atomic nucleus, in the presence of a macroscopic magnetic field, aligns itself parallel to the vector of the macroscopic magnetic field at the location of the atomic nucleus. The vector of the magnetic moment of the atomic nucleus precesses around the vector of the macroscopic magnetic field at the location of the atomic nucleus. The frequency of precession is the Larmor frequency $\omega_L$ and is proportional to the magnitude of the magnetic field strength B. The Larmor frequency is calculated according to the gyromagnetic ratio, $\omega_L = \gamma \cdot B$. $\gamma$, which is at a maximum for hydrogen nuclei. The precession of the magnetic moment of a nucleus is a magnetic alternating field at the Larmor frequency, which can induce an electrical alternating signal with the same frequency in a coil. Nuclear magnetic resonance measurement methods are measurement methods that influence the precession of atomic nuclei of a medium in the presence of a macroscopic magnetic field by a controlled magnetic field excitation means, and that evaluate the action of the influence.

Nuclear magnetic flowmeters are one example of measurement devices that use nuclear magnetic resonance. Nuclear magnetic flowmeters include nuclear magnetic measurement devices that can measure the flow rate (i.e., the flow velocity) of individual phases of a multiphase medium and the relative proportions of individual phases in the multiphase medium. Nuclear magnetic flowmeters can be used, for example, for measuring the flow rate of a multiphase medium that has been conveyed from oil sources. This medium consists essentially of the liquid phases of crude oil and salt water, and the gaseous phase natural gas. All such phases contain hydrogen nuclei, which are necessary for nuclear magnetic resonances and are excitable to different nuclear magnetic resonances.

A medium that has been conveyed from oil sources can also be measured using test separators. The conveyed medium is introduced into test separators over a time interval, wherein the test separator separates the individual phases of the medium from one another and determines the proportions of the individual phases in the medium. However, test separators, in contrast to nuclear magnetic flowmeters, are not able to reliably separate proportions of crude oil smaller than 5%. Since the proportion of crude oil of all oil sources continuously decreases, and since the proportion of crude oil of a host of oil sources is already less than 5%, at present, it is not possible to economically exploit these oil sources using test separators. In order to exploit oil sources with very small proportions of crude oil, correspondingly accurate flowmeters for mediums consisting of several phases are necessary. In particular, nuclear magnetic flowmeters are suitable for this purpose.

In nuclear magnetic flowmeters, the magnetic field, which initially aligns the magnetic moments of the nuclei of the medium and determines the Larmor frequency of precession, is generated by a magnetization device. The controlled magnetic field, which excites the aligned and precessed nuclei, can be generated by an electric coil. The coil is a component of the electrical load of the signal analyzer and the electric load is electrically connected to the signal generator of the nuclear magnetic flowmeter generating electrical excitation from the power signal line. Excitation signals oscillating at the Larmor frequency are particularly suitable for excitation. The electrical load is usually designed as a resonant circuit with an adjustable resonant frequency and an adjustable input impedance to allow for efficient transmission of power from the signal generator via the power signal line to the coil along the power signal path.

The resonant frequency of the electrical load can be attuned to the Larmor frequency of the phase of the medium to be measured for implementing the efficient transmission of power. Additionally, power adaptation can be performed in the power signal path. Power adaptation is provided by adjusting the output impedance of the signal generator, the characteristic impedance of the power signal line and the input impedance of the load to one another. A measure for power adaptation of the electrical load is the ratio between the power of the excitation signal occurring in the load and the part of the power of the occurring excitation signal reflected from the load. During power adaptation, no reflection of the excitation signal occurring in the load occurs on the load.

Signal analyzers known from the prior art, in particular for nuclear magnetic flowmeters, of the type described above have a decoupling circuit with a first directional coupler and a second directional coupler. The first directional coupler generates a first signal characterizing an excitation signal occurring in the load and the second directional coupler generates a second signal characterizing a part of the excitation signal reflected at the load. In this case, the phase position of the first signal relative to the phase position of the voltage of the excitation signal and the phase position of the second signal with respect to the phase position of the voltage of the reflected portion of the excitation signal are equal, wherein both voltages are measures for the power transmitted via the power signal path. If the output impedance of the signal generator has no reactance, which is usually the case, then in the signal analyzers known from the prior art and using conventional power signal lines, the phase difference between the first signal and the second signal needed for power adaptation is 0 degrees. Phase differences in the range of 0 degrees, however, influence evaluation by the detector.

SUMMARY OF THE INVENTION

The primary object of the present invention is to provide a signal analyzer for nuclear magnetic flowmeters. In accordance with aspects of the present invention, the signal analyzer provides for improved characteristics and for improved evaluation of the phase difference between the first signal and the second signal used for power adaptation.

The signal analyzer for nuclear magnetic flowmeters in accordance with aspects of the present invention includes a decoupling circuit having a first transformer and a second transformer. The first transformer has a primary side with an input and an output and has a secondary side with an input and an output. The second transformer has a primary side with an input and an output and has a secondary side with an input and an output. The voltage on the primary-side input with respect to the primary-side output of each transformer is in phase with the voltage at its secondary-side input with respect to its secondary-side output. The primary-side input of the first transformer is connected to the power signal line and the primary-side output of the first transformer is connected to a reference potential. The primary-side input and the primary-side output of the second transformer are connected to the power signal line and the current flowing through the power signal line flows through the primary side of the second transformer. The secondary-side input of the second transformer is connected to the reference potential and the secondary-side output of the second transformer is connected to the secondary side input of the first transformer. The first signal is applied to the secondary-side output of the first transformer and the second signal is applied to the connection of the secondary-side input of the first transformer and the secondary-side output of the second transformer.

As opposed to the signal analyzer known from the prior art (which includes two directional couplers), the decoupling circuit of the signal analyzer according to the present invention advantageously includes only one directional coupler comprising the two transformers, which reduces manufacturing effort and costs. A further advantage of the signal analyzer according to the present invention is that the phase difference between the first signal and the second signal used for power adaptation is greater than the phase difference necessary for signal analyzers known from the prior art. This provides improved evaluation of the phase difference by the same detector. If the output impedance of the signal generator has no reactance, then, in the signal analyzer according to the present invention and using conventional power signal lines, the phase difference between the first signal and the second signal used for power adaptation is 90 degrees. Phase differences in the range of 90 degrees do not influence evaluation by the detector.

Phase differences of two signals in the range of 90 degrees can be detected with higher accuracy by detectors known from the prior art than phase differences in the range of 0 degrees. In addition, conventional detectors can only detect phase differences between two signals in a range from 0 degrees to 180 degrees. Thus, in order to use such conventional detectors, it may be necessary to use an additional phase shifter that shifts the phase position between the first and the second signal.

Although nuclear magnetic flowmeters are described herein, the signal analyzer according to the present invention may still be used in other applications where a corresponding first signal and second signal are to be analyzed. The ratio of the magnitude of the first signal to the magnitude of the second signal determined by the signal analyzer according to the present invention, and the determined phase difference between the first signal and the second signal, are not limited to power adaptation, and can be used of other adaptations and analyses.

In embodiments of the signal analyzer according to the present invention, the second transformer is located before the first transformer and arranged in the direction of propagation of the excitation signal in the output signal path. Thus, the first signal runs 90 degrees ahead of the second signal at ohmic output impedance of the signal generator and ohmic input impedance of the load. To simplify the decoupling circuit, the transformation ratio of the second transformer can be the reciprocal of the transformation ratio of the first transformer. Accordingly, two identical transformers can be used wherein, in one of the two transformers, the primary side and the secondary side are exchanged with one another. Two identical transformers further reduce the cost of the signal analyzer. The secondary-side output of the first transformer can be connected to the reference potential via a first terminating resistor. The connection from the secondary-side output of the second transformer and the secondary-side input of the first transformer can be connected to the reference potential via a second terminating resistor. The value for each of the two terminating resistors is given by the characteristic impedance of the power signal line. Reflections of signals spreading in the power signal path can be avoided by choosing the values of the terminating resistors.

Further, in embodiments of the signal analyzer in accordance with the present invention, the first signal is supplied to a first signal conditioner and the second signal is supplied to a second signal conditioner. The first attenuator and a first low-pass filter are arranged in the signal path of the first signal conditioner. Accordingly, the second attenuator and a second low-pass filter are arranged in the signal path of the second signal conditioner. Both low-pass filters are designed to damp undesired frequency portions in the two signals. In embodiments, the low-pass filter is located before the attenuator in the signal path and arranged in the direction of propagation of the signal. Furthermore, advantageously for further processing, the damping of the first attenuator and the damping of the second attenuator can be attuned to one another such that the first signal at the output of the first attenuator and the second signal at the input of the second attenuator are substantially equal. For example, the transformation ratios of the two transformers can be taken into consideration when setting the damping. The magnitude of the first signal and the magnitude of the second signal are sufficiently equal when the further processing is not influenced by the remaining differences in magnitude.

Conventional detectors known from the prior art have the highest accuracy at phase differences between the first signal and the second signal in the range of 90 degrees. If a different phase difference between the first signal and the second signal is desired, a phase shifter for shifting the phase difference between the first signal and the second signal can be included in the signal path of one of the two signal conditioners. The phase shifter can also contribute to compensation of phase differences that are caused by different signal running times of the first signal and the second signal. For this reason, it is possible for the detector to operate in a highest accuracy region and when phase differences other than 90 degrees are present between the first signal and the second signal. In embodiments, the phase shifter is located after the attenuator, and arranged in the direction of propagation of the signal. Using this arrangement, the phase shifter does not need to be designed for un-damped signals. Furthermore, the signal analyzer according to the present invention makes it possible for detectors to be used for the determination of the phase difference between two signals that are formed for a phase range from 0 degrees to 180 degrees.

In a further embodiment of the signal analyzer in accordance with the present invention, the power signal line, the coil of the primary side and the coil of the secondary side of the first transformer, and the coil of the primary side and the coil of the secondary side of the second transformer are conductor paths. By implementing the power signal lines and the transformers primarily using conductor paths, the number of components is further reduced. A conventional signal analyzer typically includes a printed circuit board. In embodiments of the present invention, the conductor paths of the power signal line and the coils of the transformers can be arranged on such a printed circuit board and be manufactured in the same process, wherein the rest of the conductor paths are manufactured on the printed circuit board. This further simplifies the manufacture of the signal analyzer according to the present invention.

In embodiments of the present invention, there are a number of possibilities for designing and further developing the signal analyzer. Reference is thus made to the exemplary embodiments described below in conjunction with the accompanying drawing.

BRIEF DESCRIPTION OF THE DRAWING

The sole FIGURE shows an exemplary signal analyzer in accordance with the present invention.

DETAILED DESCRIPTION OF THE INVENTION

The FIGURE shows an exemplary signal analyzer 1 for nuclear magnetic flowmeters in accordance with the present invention. The signal analyzer 1 is arranged in a power signal path 2 between a signal generator 3 for generating an electric excitation signal and an electric load 4. The transmission of the electrical excitation signal occurs via a power signal line 5 located in the power signal path 2. The signal analyzer 1 has a decoupling circuit 6 for decoupling a first signal $s_1$ characterizing the excitation signal occurring in the load 4 and for decoupling a second signal $s_2$ characterizing part of the excitation signal reflected at the load 4. Furthermore, the signal analyzer 1 has is a first attenuator 7 and a second attenuator 8, as well as a detector 9 for determining the ratio r of the magnitude of the second signal $s_2$ in relation to the magnitude of the first signal $s_1$ and for determining the phase difference $\Delta\alpha$ between the first signal $s_1$ and the second signal $s_2$.

The decoupling circuit 6 of the signal analyzer 1 according to the present invention has a first transformer 10 and a second transformer 11. The first transformer 10 has a primary side 12 with an input 13 and an output 14, and a secondary side 15 with an input 16 and an output 17. The second transformer 11 has a primary side 18 with an input 19 and an output 20, and a secondary side 21 with an input 22 and an output 23. The primary-side coils and the secondary-side coils of the two transformers 10, 11 are oriented and coupled by respective magnetic flows. That is, the voltage $U_{11}$ on the primary side 12 of the first transformer 10 is in phase with voltage $U_{12}$ on the secondary side 15 of the first transformer 10 and the voltage $U_{21}$ on the primary side 18 of the second transformer 11 is in phase with the voltage $U_{22}$ on the secondary side 21 of the second transformer 11.

The primary-side input 13 of the first transformer 10 is connected to the power signal line 5 and the primary-side output 14 of the first transformer 10 is connected to a reference potential 24. The primary-side input 19 and the primary-side output 20 of the second transformer 11 are connected to the power signal line 5, and the current flowing through the power signal line 5 flows completely through the primary side 18 of the second transformer 11. The secondary input 22 of the second transformer 11 is connected to the reference potential 24 and the secondary output 23 of the second transformer 11 is connected to the secondary input 16 of the first transformer 10. The first signal $s_1$ is applied to the secondary-side output 17 of the first transformer 10 and the second signal $s_2$ is applied to the connection of the secondary-side input 16 of the first transformer and the secondary-side outlet 23 of the second transformer.

The second transformer 11 is arranged in the direction of propagation of the excitation signal in the power signal path 2 before the first transformer 10. Accordingly, the first signal $s_1$ is a measure for the voltage of the excitation signal occurring in the load 4 and the signal $s_2$ is a measure for the current of the part of the excitation signal reflected at the load 4. Consequently, the phase difference between the first signal $s_1$ and the second signal $s_2$ at an ohmic output resistance of the signal generator 3 and an ohmic input resistance of the load is +90 degrees.

The transformation ratio $n_2$ of the second transformer 11 is the reciprocal of the transformation ratio $n_1$ of the first transformer 10. Consequently, the first transformer 10 and the second transformer 11 are identical except for swapped primary sides and secondary sides. Costs are saved by using two identical transformers. The number of coils of the secondary side 15 of the first transformer 10 and the number of coils of the primary side 18 of the second transformer 11 is 1. The number of coils of the primary side 12 of the first transformer 10 and the number of coils of the secondary side 21 of the second transformer 11 is 15. Thus, the transformation ratio of the first transformer 10 is $n_1=15$ and the transformation ratio of the second transformer 11 is $n_2=1/15$. By choosing these particular transformation ratios $n_1$, $n_2$ the couplings are optimal.

The secondary output 17 of the first transformer 10 is connected to the reference potential 24 via a first terminating resistor $R_1$ and the connection from the secondary side output 23 of the second transformer 11. The secondary-side input 16 of the first transformer 10 is connected to the reference potential 24 via a second terminating resistor $R_2$. The two terminating resistors $R_1$, $R_2$ each match a value of the characteristic impedance of the power signal line 5. Reflections of signals spreading to the power signal path 2 can be avoided using the terminating resistors $R_1$, $R_2$.

The first signal $s_1$ is supplied to a first signal conditioner 25 and the second signal $s_2$ is supplied to a second signal conditioner 26. The first signal conditioner 25 includes the first attenuator 7 and a first low-pass filter 27. The second signal conditioner 26 comprises the second attenuator 8, a second low-pass filter 28 and a phase shifter 29. The first low-pass filter 27 and the second low-pass filter 28 are used for damping of unwanted frequency components in the two signals $s_1$, $s_2$. In the direction of flow of the signal, the first attenuator 7 follows the first low-pass filter 27 in the signal path of the first signal conditioner 25. In the direction of flow of the signal, the second attenuator 8 follows the second low-pass filter 28 and the phase shifter 29 follows the attenuator 8 in the signal path of the second signal conditioner 26.

The first signal $s_1$ conditioned by the first signal conditioner 25 and the second signal $s_2$ conditioned by the second signal conditioner 26 are fed to the detector 9. The detector 9 determines the ratio of the magnitude of the conditioned first signal $s_1$ to the magnitude of the conditioned second signal $s_2$ and determines the phase difference between the conditioned first signal $s_1$ and the conditioned second signal $s_2$.

What is claimed is:

1. A signal analyzer, comprising:
a power signal line in a power signal path for the transmission of electrical signals;
a decoupling circuit that decouples a first signal characterizing an excitation signal occurring in a load and that decouples a second signal characterizing a part of the excitation signal reflected at the load;
a first attenuator;
a second attenuator;
a detector that determines the ratio of a magnitude of the first signal to a magnitude of the second signal and that determines a phase difference between the first signal and the second signal,
wherein:
the decoupling circuit includes a first transformer and a second transformer;
the first transformer includes a primary side having a primary-side input and a primary-side output;
the first transformer includes a secondary side having a secondary-side input and a secondary-side output;
the second transformer includes a primary side having a primary-side input and a primary-side output;
the second transformer includes a secondary side with a secondary-side input and a secondary-side output;
the voltage on the primary-side input of the first transformer with respect to the primary-side output of the first transformer is in phase with the voltage at the secondary-side input of the first transformer with respect to the secondary-side output of the first transformer;
the voltage on the primary-side input of the second transformer with respect to the primary-side output of the second transformer is in phase with the voltage at the secondary-side input of the second transformer with respect to the secondary-side output of the second transformer;
the primary-side input of the first transformer is connected to the power signal line;
the primary-side output of the first transformer is connected to a reference potential;
the primary-side input and the primary-side output of the second transformer are connected to the power signal line;
the current flowing through the power signal line flows through the primary side of the second transformer;
the secondary-side input of the second transformer is connected to the reference potential;
the secondary-side output of the second transformer is connected to the secondary-side input of the first transformer;
the first signal is applied to the secondary-side output of the first transformer; and
the second signal is applied to the connection of the secondary-side input of the first transformer and the secondary-side output of the second transformer.

2. The signal analyzer according to claim 1, wherein:
the second transformer is arranged in the direction of propagation of the excitation signal in the power signal path; and
the second transformer is located before the first transformer in the power signal path.

3. The signal analyzer according to claim 1, wherein a transformation ratio of the second transformer is a reciprocal of a transformation ratio of the first transformer.

4. The signal analyzer according to claim 1, wherein:
the secondary-side output of the first transformer is connected to the reference potential via a first terminating resistor; and
the connection from the secondary-side output of the second transformer and the secondary-side input of the first transformer is connected to the reference potential via a second terminating resistor.

5. The signal analyzer according to claim 4, wherein the first terminating resistor and the second terminating resistor match a value of the characteristic impedance of the power signal line.

6. The signal analyzer according to claim 1, wherein:
the first signal is supplied to a first signal conditioner;
the second signal is supplied to a second signal conditioner;
the first attenuator and a first low-pass filter are arranged in a signal path of the first signal conditioner;
the second attenuator and a second low-pass filter are arranged in a signal path of the second signal conditioner; and
the first low-pass filter and the second low-pass filter damp frequency components in the signal path of the first signal conditioner and the signal path of the second signal conditioner, respectively.

7. The signal analyzer according to claim 6, wherein:
the first low-pass filter is arranged in the signal path of the first signal condition in the direction of propagation of the signal before the first attenuator; and
the second low-pass filter is arranged in the signal path of the second signal condition in the direction of propagation of the signal before the second attenuator.

8. The signal analyzer according to claim 6, wherein the damping of the first attenuator and the damping of the second attenuator, based on the respective transformation ratios of the first transformer and the second transformer, are attuned to one another such that the first signal at the output of the first attenuator and the second signal at the output of the second attenuator are substantially equal.

9. The signal analyzer according to claim 6, wherein:
a phase shifter is arranged in the signal path of one of the first signal conditioner and the second signal conditioner, and
the phase shifter varies the phase difference between the first signal and the second signal.

10. The analyzer according to claim 9, wherein the phase shifter is arranged in the direction of propagation of the signal after the attenuator.

11. The analyzer according to claim 1, wherein the detector determines phase differences of two signals in the phase range from 0 degrees to 180 degrees.

12. The signal analyzer according to claim 1, wherein the power signal line, a coil of the primary side of the first transformer, a coil of the secondary side of the first transformer, a coil of the primary side of the second transformer, and a coil of the secondary side of the second transformer are conductor paths.

* * * * *